(12) United States Patent
Wang et al.

(10) Patent No.: US 7,318,291 B2
(45) Date of Patent: Jan. 15, 2008

(54) HYGIENICAL SHOES WITH MOBILE MAGNET PIECE

(76) Inventors: Jian Wang, No. 6, Rongyuan Road, Huayuan Industry Park, Nakai District, Tianjin 300384 (CN); Huimin Gong, No. 6, Rongyuan Road, Huayuan Industry Park, Nakai District, Tianjin 300384 (CN)

( * ) Notice: Subject to any disclaimer, the term of this patent is extended or adjusted under 35 U.S.C. 154(b) by 0 days.

(21) Appl. No.: 11/177,312

(22) Filed: Jul. 11, 2005

(65) Prior Publication Data

US 2006/0005427 A1    Jan. 12, 2006

(51) Int. Cl.
*A61F 5/14*   (2006.01)

(52) U.S. Cl. ........................................ 36/141
(58) Field of Classification Search ............... 36/141
See application file for complete search history.

(56) References Cited

U.S. PATENT DOCUMENTS

| | | | |
|---|---|---|---|
| 2,734,286 A * | 2/1956 | Anson ........................ | 36/141 |
| 4,033,054 A | 7/1977 | Fukuoka et al. | |
| 6,360,457 B1 * | 3/2002 | Qui et al. .................... | 36/140 |
| 2004/0230139 A1 * | 11/2004 | Chang ........................ | 601/15 |

FOREIGN PATENT DOCUMENTS

| | | |
|---|---|---|
| CN | 1 067 799 A | 1/1993 |
| CN | 1 113 817 A | 12/1995 |
| CN | 1 142 304 A | 2/1997 |
| EP | 383685 A1 * | 8/1990 |
| EP | 470767 A1 * | 2/1992 |
| JP | 2002 177004 A | 6/2002 |

* cited by examiner

*Primary Examiner*—Ted Kavanaugh
(74) *Attorney, Agent, or Firm*—Baker & Hostetler LLP

(57) ABSTRACT

A kind of hygienical shoes with mobile magnet piece, which can produce the static and dynamic magnet field for the sole of foot of human body, especially it can carry out the magnetotherapy for the sole of foot with take advantage of the static and dynamic magnet field generated respectively at sole when human body stops and walks. Wherein the shoe sole includes a lower sole and a insole covering on the upper surface of the lower sole; the grooves is set on the upper surface of insole, and the mobile magnet pieces is provided on the bottom of groove. When the shoes according to the present invention are wore on foot for walking, as the foot lift up and fall down, the front and back portions of grooves will change their relative position repeatedly, and the magnet pieces in the grooves will move fore-and-aft depending on the obliquity of the bottom of groove under the effect of gravity, which result in the movement of magnet field, i.e. the dynamic magnet field. In resting state, the magnet pieces generate the static magnet field. When human body stops and walks, the shoes according to the present invention perform the magnetotherapy for the sole of foot with two forms of magnetic field thereby improving the effect of magnetotherapy in the sole of foot.

11 Claims, 2 Drawing Sheets

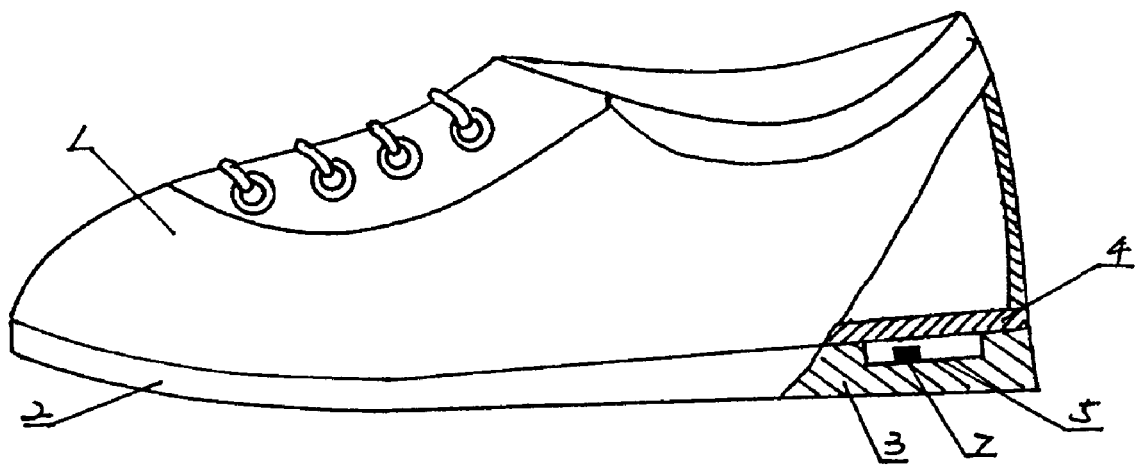
Fig.1 (drawing of abstract)
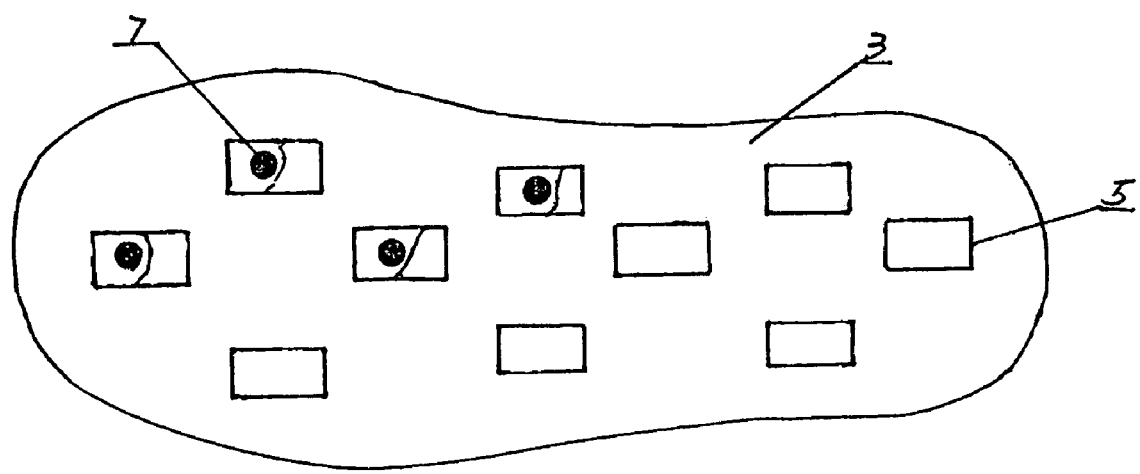
Fig.2

HYGIENICAL SHOES WITH MOBILE MAGNET PIECE

CROSS REFERENCE TO RELATED APPLICATIONS

This application claims priority to Chinese Application Serial No. 200420029313.1 filed Jul. 12, 2004 entitled, THE HYGIENICAL SHOES WITH MAGNET PIECE, the disclosure of which is incorporated by reference in its entirety.

FIELD OF THE TECHNOLOGY

This invention relates to a kind of hygienical shoes. More particularly, the hygienical shoes with mobile magnet piece.

BACKGROUND OF THE INVENTION

According to the meridian doctrine of the traditional Chinese medicine, there are some important meridians, such as the spleen channel, the urinary bladder channel, the stomach channel, the kidney channel, the liver channel and the gallbladder meridian, etc, and constitute a lot of important acupuncture points in the sole of foot. From the long-term practice of the traditional Chinese medicine, it has been proved that the massaging and stimulating for the meridians and acupuncture points in the sole of foot may dredge human body's meridians and activate human body's potential to attain the effect of dispelling illness, activating the channels and warming the internal organs. Therefore, "the reflect zone massotherapy of human body's thenar" is widely spread, and become a health protection method and an auxiliary therapy for illness.

Recently, with the development of science and technology, a variety of hygienical shoes are provided to achieve the goal of massaging and stimulating the meridians and acupuncture points in the sole of foot. For example, the magnet piece is provided onto the insole so that the magnet field can stimulate a certain acupuncture point in the sole of foot. Though this king of hygienical shoes can achieve the goal of magnetotherapy for the acupuncture point, the fixed magnet piece set onto the insole generates only static magnet field for a certain acupuncture point in the sole of foot of human body, not the dynamic magnet field. This restricts the effect of magnetotherapy. Thereby, this kind of hygienical shoes has some limitations.

In addition, in order to improve the magnetotherapy's effect in the sole of foot and generate dynamic magnet field in the sole of foot of human body, some shoes are provided with coils at sole, thus when the alternating current flow through the coils, the pulse magnet field for performing the magnetotherapy of dynamic magnet field in the sole of foot of human body is generated in the sole of foot of human body. This kind of magnetotherapy shoes improve the effect of magnetotherapy, but the alternating current flowing through the sole's coil is necessary for the generation of dynamic magnet field, so this kind of shoes can not be used in walking, but carry out the magnetotherapy of dynamic magnet field in a fixed position only after settling in a certain place, pulling out the wire with a plug and inserting the plug into the power outlet.

All of the above mentioned hygienical shoes can not carry out the magnetotherapy for the sole of foot with the static and dynamic magnet field generated respectively at sole due to the rest and movement of foot and shoes when human body stops and walks.

SUMMARY OF THE INVENTION

The present invention directs to a kind of hygienical shoes with mobile magnet piece which can carry out the magnetotherapy for the sole of foot with the static and dynamic magnet field generated respectively at sole due to the rest and movement of foot and shoes when human body stops and walks.

A shoe according to the present invention comprises a vamp and a sole, as shown in FIG. 1. The sole comprises a lower sole and an insole covering over the upper surface of the lower sole. The upper surface of lower sole is provided with grooves, and the mobile magnet pieces are placed on the bottom of grooves, as shown in FIG. 2.

According to the present invention, there may be several grooves distributed all over the upper surface of lower sole or allocated only in the predetermined positions.

The bottom of the grooves according to the present inventions may be a horizontal plane or a inclined plane.

According to the present invention, a lining piece is set along the inner side of the groove, which is a smooth-faced sheet making from a hard elastic material. Both ends of the lining piece are overlapped a short part at the longitudinal side of the groove.

The magnet pieces of the present invention may be bead-like, columnar or round-sheet shapes.

In walking with the shoes according to the present invention, when the foot lifts up to move forward, as the front of the shoes move upwards and onwards, the magnet piece on the bottom of groove will slide backwards to the back of groove along the surface of groove's bottom; and when the foot lifts up again after falling down to ground, the heel lifts up and at the same time the magnet piece in the groove will slide to the front portion of groove along the bottom surface of groove. As such, the foot lifts up and falls down repeatedly and moves forward, the front and rear portions of grooves change their relative position continuously, and the magnet pieces in the groove will slide or tumble depending on the obliquity of the bottom of groove under the effect of gravity. The fore-and-aft movement of magnet piece cause the movement of the magnet field, which in turn form the dynamic magnet field. When the dynamic magnet field acts on the sole of foot of human body, the massage of dynamic magnet field enhances the effect of magnetotherapy for the sole of foot.

When resting, the static magnet field of magnet piece may carry out the magnetotherapy of static magnet field for the sole of foot of human body.

In a word, the present invention is a kind of hygienical shoes with mobile magnet pieces, which can carry out the magnetotherapy for the sole of foot of human body with the static and dynamic magnet field generated respectively at sole due to the rest and movement of foot and shoe when human body stops and walks.

BRIEF DESCRIPTION OF THE DRAWINGS

FIG. 1 is a whole schematic drawing of the present invention.

FIG. 2 is a top view of the lower sole of the present invention.

In the figures: 1-vamp, 2-sole, 3-lower sole, 4-insole 5-groove, 6-lining piece, 7-magnet piece, 8-overlapped part.

DETAILED DESCRIPTION OF THE INVENTION

EXAMPLE 1

Figure 3:
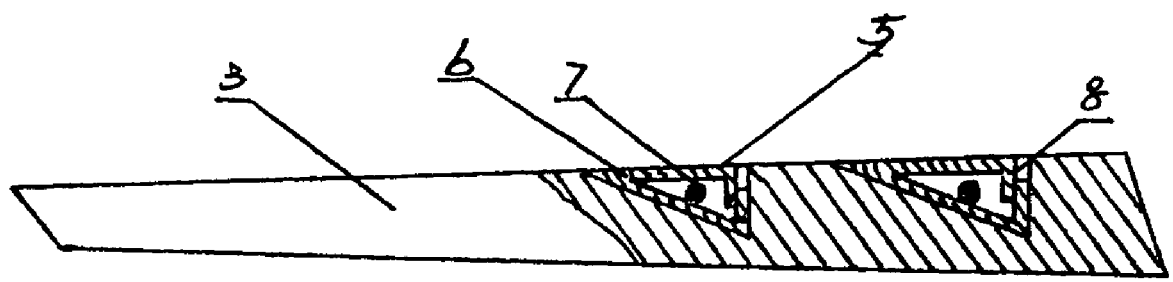
FIG. 3 is a schematic drawing of the lower sole of an embodiment of the present invention.
Figure 4:
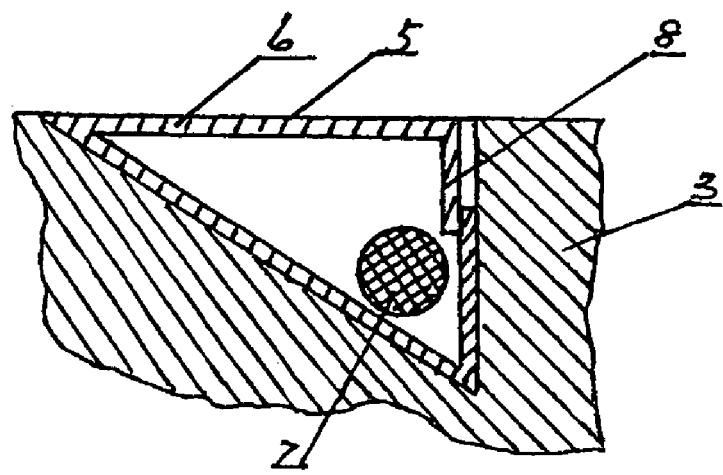
FIG. 4 is a schematic drawing of the groove in the lower sole, the lining piece, the magnet piece and the overlapped part according to an embodiment of the present invention.

A travel shoe adopting the present invention, comprising a vamp 1 made from the sheepskin, and a sole 2 formed by combination of an insole 4 and a lower sole, wherein the insole 4 is made from cowskin and the lower sole is made from polyurethane; 3×2 (6 in all) grooves 5 are provided on the upper surface of lower sole 3; the bottom of grooves 5 are inclined planes with higher front portion and lower rear portion; a lining piece 6 is set in the groove 5 along the upper, lower and back inside thereof, the ends of the lining piece at the back side of the groove are not linked up but overlapped a short part in longitudinal direction; and a mobile conglobate magnet piece 7 is placed on the inner surface of inside lining piece 6 of the groove's bottom, as shown in FIG. 3 and FIG. 4.

When the shoes according to the present invention is wore on foot, in resting, the conglobate magnet piece 7 will slide to the lower position of the inclined bottom of groove 5, i.e. the rear portion of groove's bottom, along the inner surface of lining piece under the gravity; and the static magnet field of the conglobate magnet piece can stimulate directly the sole of foot of human body.

While in walking, the heel lifts up after the footfalls down to the ground, and at this time, the sole 2 is in the state of lower front and higher back, the conglobate magnet piece 7 rested on the lining piece 6 of the back portion of the groove bottom will tumble to the front portion of groove bottom along the inner surface of lining piece 6 of the groove bottom under the gravity; and when moving forwards, the groove 5 produces a forward acceleration along with the foot's movement, and due to the very small friction coefficient between the lining piece 6 and the conglobate magnet piece 7, the conglobate magnet piece 7 placed on the lining piece 6 of the front portion of groove bottom will slide to the lower portion of groove bottom 8 of the groove 5 under the backward counterforce and the gravity.

Whenever the foot falls down to the ground, the lower sole 3 made from polyurethane will occur the compression deformation under the vertical downward force. At the same time, the longitudinal overlapped part 8 of the lining piece 6 will become shorter by interleaving along with the deformation of the lower sole 3, thereby can not press against the foot.

Again and again, whenever the foot move forward a step, the conglobate magnet piece 7 in each groove 5 of the lower sole 3 will move fore-and-aft one time, and at the same time, bring the movement of magnet field one time. The dynamic magnet field moving to and fro can massage and stimulate the sole of foot of human body directly.

According to the present invention, the static and dynamic magnet field contacts the sole of foot of human body directly and carries out the magnetotherapy for the sole of foot of human body with two forms of magnetic field, which improves the magnetotherapy's effect of the sole of foot. In particular, the dynamic magnet field, which is generated by the shoes itselves along with the motion of the foot and shoes when human body is walking, can be used to carry out the magnetotherapy for the sole of foot of human body.

We claim:

1. A hygienical shoe with mobile magnet pieces, comprising a vamp and a sole, wherein the sole includes a lower sole and an insole covering on the upper surface of the lower sole; wherein several grooves are set on the upper surface of the lower sole, wherein each groove forms a space and a mobile magnet piece is placed on the bottom of each groove, wherein each groove is larger than its respective mobile magnet piece, and each mobile magnet piece can move fore-and-aft in its space formed by the groove.

2. The hygienical shoe with mobile magnet pieces as set forth in claim 1, wherein a lining piece is set along the inner side of the groove, which is a smooth-faced sheet made from a hard elastic material.

3. The hygienical shoe with mobile magnet pieces as set forth in claim 2, wherein both ends of the lining piece are overlapped by a short part at the longitudinal side of the groove.

4. The hygienical shoe with mobile magnet pieces as set forth in claim 1, wherein the groove's bottom is horizontal.

5. The hygienical shoe with mobile magnet pieces as set forth in claim 1, wherein the groove's bottom is inclined.

6. The hygienical shoe with mobile magnet pieces as set forth in claim 1, wherein the magnet piece has a bead-like shape.

7. The hygienical shoe with mobile magnet pieces as set forth in claim 1, wherein the magnet piece has a columnar shape.

8. The hygienical shoe with mobile magnet pieces as set forth in claim 1, wherein the magnet piece has a flat round shape.

9. The hygienical shoe with mobile magnet pieces as set forth in claim 1, wherein the lower sole extends fore-and-aft from a front thereof to a rear thereof and the cross section of each groove space is elongated in the fore-and-aft direction, thereby permitting movement of the mobile magnet piece inside of the opening in the fore-and-aft direction.

10. The hygienical shoe with mobile magnet pieces as set forth in claim 9, wherein the opening has an internal length in the fore-and-aft direction that is greater than a length of the mobile magnet piece in the fore-and-aft direction, permitting movement of the mobile magnet piece in the fore-and-aft direction inside the opening.

11. The hygienical shoe with mobile magnet pieces as set forth in claim 10, wherein each groove has only a single mobile magnet piece therein.

* * * * *